United States Patent [19]

Deka

[11] Patent Number: 4,976,150
[45] Date of Patent: Dec. 11, 1990

[54] ULTRASONIC TRANSDUCERS

[75] Inventor: Mitrajyoti Deka, Bethlehem, Pa.

[73] Assignee: Bethlehem Steel Corporation

[21] Appl. No.: 361,679

[22] Filed: Jun. 2, 1989

Related U.S. Application Data

[63] Continuation of Ser. No. 947,790, Dec. 30, 1986, abandoned.

[51] Int. Cl.$^5$ ............................................. G01N 29/00
[52] U.S. Cl. ......................................................... 73/644
[58] Field of Search ................ 73/159, 597, 598, 644; 310/335, 339, 342; 367/152

[56] References Cited

U.S. PATENT DOCUMENTS

| | | | |
|---|---|---|---|
| 3,378,705 | 4/1968 | Bacon | 73/644 |
| 3,928,777 | 12/1975 | Massa | 310/8.2 |
| 4,211,948 | 7/1980 | Smith et al. | 310/322 |
| 4,291,577 | 9/1981 | Baum et al. | 73/597 |
| 4,297,607 | 10/1981 | Lynnworth et al. | 310/334 |
| 4,519,249 | 5/1985 | Hunt | 73/596 |
| 4,523,122 | 6/1985 | Tone et al. | 310/334 |
| 4,594,897 | 6/1986 | Bantz | 73/600 |
| 4,672,591 | 6/1987 | Breimesser et al. | 367/152 |
| 4,674,334 | 1/1987 | Chimenti et al. | 73/627 |

FOREIGN PATENT DOCUMENTS

| | | | |
|---|---|---|---|
| 838402 | 11/1978 | U.S.S.R. | 73/159 |

OTHER PUBLICATIONS

Lawrence C. Lynnworth, "Ultrasonic Impedance Matching from Solids to Gases", 1965, pp. 37–48.
V. I. Zaklyukovskii and G. T. Kartsev, "Use of Piezoelectric Transducers for Contactless Ultrasonic Product Insepction", Soviet NDT, 1978, pp. 211–216.
M. Luukkala, P. Heikkila and J. Surakka, "Plate Wave Resonance-A Contactless Test Method", Ultrasonics, 1971, pp. 201–208.
Emmanuel P. Papdakis, "Ultrasonic Methods for Modulus Measurement in Paper", Tappi, 56, No. 2, 1973, pp. 74–77.
Ming T. Lu, "On Line Measurement of Strength Characteristics of a Moving Sheet", Tappi, 58, No. 6, 1975, pp. 80–81.
C. C. Habeger, R. W. Mann & G. A. Baum, "Ultrasonic Plate Waves in Paper", Ultrasonics, 1979, pp. 57–62.
Y. Bar-Cohen, "NDE of Fiber Reinforced Composite Materials—A Review", Materials Evaluation, 44, 1986.
T. S. Jones, "Inspection of Composites Using the Automated Ultrasonic Scanning System (AUSS)", Materials Evaluation, 43, 1985.

Primary Examiner—Jerry W. Myracle
Attorney, Agent, or Firm—Pennie & Edmonds

[57] ABSTRACT

A transducer including a piezoelectric layer and a coupling medium in the form of matching layers for matching the transducer impedance to that of air. The transducer may be used in the measurement of the strength of paper, the detection of defects in a multilayer composite material and the measurement of their properties, among other uses.

9 Claims, 3 Drawing Sheets

ULTRASONIC TRANSDUCERS

This is a continuation of application Ser. No. 06/947,790 filed Dec. 30, 1986, now abandoned.

TECHNICAL FIELD

The invention relates to a transducer assembly and a method of use of the transducer assembly in a system for inspecting quality and measuring both the dimensions and properties of materials. The method is carried out through use of ultrasonics, an air medium to conduct ultrasonic energy to the material and receive emitted energy from the material undergoing inspection and measurement and a coupling medium for matching transducer impedance to that of air. Particular uses of the invention are in the measurement of the strength of paper, the detection of defects in multilayer composite materials and the measurement of the dimension of materials, among possible other uses.

BACKGROUND ART

It is known in the prior art that ultrasonic energy may be coupled into an object using an ultrasonic transducer applied to the surface of the object. It is also known that a coupling material must be located between the transducer and the surface of the object if the soundwave is to be coupled into the object efficiently.

The conventional type coupling methods are not practicable under all circumstances. Thus, conventional coupling methods are considered not to be practical or capable of use under circumstances that the object, such as a bloom or slab of metal undergoing test is moving in an on-line plant application at a high rate of speed. Under these particular conditions, among other possible conditions, non-contact coupling techniques and methods generally are required to transmit and receive the ultrasonic signal.

Two well known techniques and methods of non-contact generation and reception of ultrasound utilize an electromagnetic acoustic transducer (EMAT) and a laser. Both of these non-contact techniques, however, are considered to present certain problems and disadvantages. For example, the EMAT requires a close proximity, possibly in the range of less than about 0.1 inch, between the material and transducer. In many industrial applications, a sensor will be subject to damage if positioned at such a close range of proximity to material undergoing test. Further, an EMAT can only be used on metal base materials, and the EMAT is a poor receiver of ultrasound. On the other hand, the laser which may be more distantly spaced from the material, for example, spaced at a distance possibly of several feet, requires for use product surface preparation and a high power confined beam to generate ultrasound efficiently. The use of high power lasers in a plant environment may create potential safety problems.

The prior art includes further disclosures of an air coupled ultrasonic transducer wherein the acoustic impedance of the transducing element is matched to the acoustic impedance of air. Thus, the prior art includes a paper, entitled "Ultrasonic Impedance Matching From Solids to Gases", by Lawrence C. Lynnworth, which describes that one quarter wavelength thickness matching layers may increase intensity of ultrasound transmitted from solids to gases. Lynnworth discloses the use of combined resonant- and nonresonant matching layers. The resonant layers are one quarter wavelength, and the nonresonant layers are some wavelength other than one quarter wavelength. In order to approach maximum gain, possible by impedance matching, Lynnworth describes new acoustic materials having impedances between the impedances of gases and solids. To this end, Lynnworth discusses matching layers of compressed gas and water. These matching layers are not considered suitable for durable industrial apparatus. It is also considered that the use of diaphragms to contain the fluids undoubtedly will reduce the efficiency that otherwise may have been realized by the Lynnworth apparatus.

Another paper of the prior art, entitled "Use of Piezoelectric Transducers for Contactless Ultrasonic Product Inspection", by V. I. Zaklynkovskii and G. T. Kartsev, describes an air coupled transducer for non-contact inspection of materials. According to the authors, inspection is carried out by coupling ultrasound using a single one quarter wavelength matching layer in front of the piezoelectric layer and a semi-infinite damping layer in back of the piezoelectric layer. The technique and apparatus is considered to suffer from low efficiency, and the low operating frequency of the apparatus, up to about 50 KHz, is also considered to be a drawback.

U.S. Pat. No. 3,928,777 to Frank Massa describes a transducer somewhat similar to the transducer described by Zaklynkovskii et al although having an operating frequency of up to about 280 KHz. According to Massa, a one quarter wavelength layer of potting compound is used as the matching layer. It is considered, however, that potting compounds, usually resilient in nature, are not efficient conductors of ultrasound. Further, the impedance of resilient potting compounds is significantly different from the impedance required for good matching.

A further disclosure of the prior art is U.S. Pat. No. 4,594,897 to Walter J. Bantz. In the patent, Bantz describes a transducer consisting of a layer of piezoelectric material and two matching layers. The piezoelectric layer operates at other than one half wavelength resonance. The first matching layer of the coupling medium also operates at other than one quarter wavelength while the second matching layer of the coupling medium operates at one quarter wavelength resonance at the operating frequency determined by the composite of the piezoelectric layer and the first layer. According to Bantz, the first matching layer consists of two layers of different materials. In order to operate at frequencies on the order of 500 KHz, the individual layers are required to be thin and of precise thickness throughout. While the Bantz apparatus operates substantially satisfactorily, the specific criteria of thickness and non-uniformity of the adhesive materials required to bond the four layers together may introduce a considerable measure of impedance mismatch and loss of efficiency.

A further patent of the prior art is U.S. Pat. No. 4,523,122 to Masayuki Tone, Tsutomu Yano and Koetsu Saito (hereafter "Tone et al.") which describes the matching of acoustic impedance of the piezoelectric source to air by applying either one or two matching layers of special materials, such as a porous polymer film or a composite material comprising thermally expanded resin microspheres to the transducer face. Tone et al. accomplish this by providing materials containing microspheres of specific size and distribution dispersed in the cured product. It is considered that the development of these special materials with specific impedance characteristics is time consuming and difficult, and it is known that porous materials exhibit high absorption of ultrasound. Thus, in all likelihood the impedance matching scheme of Tone et al. will sacrifice a substantial measure of transducer efficiency.

The prior art also provides a recognition that the velocity of ultrasonic waves is related to Young's modulus, and that there is a relationship between Young's modulus and the tensile strength of paper. This recognition may be drawn from several articles including an article "Plate Wave Resonance—A Contactless Test Method", by M. Luukkala, P. Heikkila and J. Surakka; an article "Ultrasonic Methods For Modulus Measurement In Paper", by Emmanuel P. Papadakis; an article "On-line Measurement Of Strength Characteristics Of A Moving Sheet", by Ming T. Lu; an article "Ultrasonic Plate Waves In Paper", by C. C. Habeger, R. W. Mann and G. A. Baum; and U.S. Pat. No. 4,291,557 to G. A. Baum and C. C. Habeger. The Baum et al. patent also describes a method of monitoring paper strength in real-time during the papermaking process. The method is carried out by mounting a transducer assembly to a wheel/roll. The transducer assembly is mounted on the papermaking machine so that it contacts the paper web to excite and detect plate waves of a specific frequency. While the method demonstrates that an on-line measurement of paper strength is possible the method is not without its disadvantages. To this end, the system consists of a large mechanical assembly which contacts the paper web. Therefore, it is considered necessary to limit use of the method in testing high strength papers, such as Kraft paper. In addition it is considered difficult to maintain synchronization between the transmit and receive transducer assemblies to obtain reliable long term mechanical/electrical operation, particularly when the wheel/roll must rotate at line speeds up to about 6000 feet per minute.

The present invention distinguishes from the disclosures of the patents and articles discussed above in that the ultrasonic transducer configuration of the invention provides greater efficiency of operation using impedance matching materials that are readily available. To this end, the invention uses two matching layers, each consisting of a single layer capable of vibrating in a thickness mode of vibration or in multiple modes of vibration. As the invention will be discussed, the first matching layer is intended to match the impedance of the piezoelectric layer to that of the second layer, providing an ultrasonic transducer having a higher efficiency at an operating frequency up to about 500 KHz.

The impedance matching techniques addressed in the disclosures of the patents and articles couple energy to air from a piezoelectric layer vibrating primarily in the thickness mode. The invention, on the other hand relates to a piezoelectric layer that vibrates at multiple modes at a single frequency. It has been found that significantly higher energy levels may be coupled to air when a piezoelectric layer vibrating in multiple modes is bonded to the impedance matching layer. A transducer of almost twice the efficiency of transducers operating only in the thickness mode has been demonstrated in effective operating ranges up to about 170 KHz.

SUMMARY OF THE INVENTION

The invention relates to a transducer assembly and system approaches for the ultrasonic inspection of a sheet material to determine quality, and the measurement of both dimensions and properties. According to the invention ambient air is used to conduct ultrasonic energy to the sheet material as well as to conduct ultrasonic vibrations from the sheet material to be received by the transducer assembly. The system approaches as will be discussed utilize a transducer assembly in a non-contact position, for example, a position located about one inch or more removed from the sheet material under test.

The transducer assembly includes a piezoelectric layer and a coupling medium for coupling ultrasonic energy under conditions of high efficiency in transmission and high sensitivity in reception. In a preferred aspect of the invention the coupling medium includes a first and second matching layer, with the second matching layer being of one quarter wavelength, while the first matching layer may be of one quarter wavelength or some other wavelength. Each matching layer may be chosen from readily available materials. The first matching layer may be formed of acrylic sheet (PLEXIGLASS), an acrylic resin (LUCITE), nylon and polystyrene, and functions to simulate an intermediate impedance which is matched by the second matching layer to the impedance of air. The second matching layer may be formed of a closed cell foam including one of polystyrene, polyurethane and other thermosetting resins that may be foamed, such as lucite and nylon. A polystyrene foam has been found to provide an impedance match for transmission/reception coupling to ambient air with high efficiency and high sensitivity. Although not limited thereto the piezoelectric material may have an acoustic impedance of about $3 \times 10^7$ PaS/M, the first matching layer may have an acoustic impedance of about $3.1 \times 10^6$ PaS/M, and the second matching layer may have an acoustic impedance of about $1.1 \times 10^4$ PaS/M.

The system approaches generally comprise a source of an oscillatory burst of acoustic energy generating a wave mode which propagates toward the sheet material under test in a non-contact mode of operation and one or more transducer assemblies of the type heretofore discussed located to respond to ultrasonic vibrations emitted from the sheet material. The system approaches, further, include suitable electronics for processing a signal representative of the ultrasonic vibrations received in the detection of defects in a sheet material in the form of a multilayer composite, and measurement of the dimension and strength of sheet material, such as paper in web form mounted for movement past the transducer assemblies. With regard to the sheet material in the form of the multilayer composite, it likewise is adapted for movement, a movement which may be in various directions within an X-Y coordinate system for purposes of presentation of various regions of the multilayer composite to the transducer assemblies for test.

According to the invention, the testing of a paper sheet material may be carried out by locating a transducer assembly serving as a source of ultrasonic acoustic energy which propagates toward one side or the other of the web of paper, and locating one or more transducer assemblies in a spaced relationship (in the direction of movement of the paper or in the opposite direction) direction on the same or different side to receive ultrasonic vibrations emitted from the paper. As will be discussed hereafter, the testing technique is able to develop data relative to the velocity of ultrasonic vibrations in the paper. This data may be used to calculate paper strength.

Also, according to the invention, testing of paper sheet material may be carried out as the paper sheet material moves linearly, and it may be carried out with the transducer assemblies disposed adjacent support rolls for the paper sheet material which serve to move the paper sheet material in a curved pass. By locating receiver transducer assemblies in both the machine direction, as discussed, and in a direction normal thereto strength of paper determinations may be derived in both directions. Additionally, the data may be used for determination of measurement, squareness of paper, and so forth.

In the testing technique for testing defects in a sheet material in the form of a multilayer composite, defects may be determined by comparing a signal of a receiver transducer representing ultrasonic vibrations emitted from the sheet material to that of a reference. The technique may be carried out with a single transducer assembly having capability of generating a wave mode which propagates toward the sheet material, and a capability of receiving ultrasonic vibrations emitted from the body. The technique may also be carried out with a pair of transducer assemblies serving a transmitter and a receiver transducer, respectively. The transducer assemblies are located with respect to the sheet material, on either the same or opposite sides, so that the generated acoustic energy wave mode will propagate toward the sheet material and the receiver transducer will respond to ultrasonic vibrations emitted from the body.

It is contemplated that the generated acoustic wave mode may be deflected by a deflector toward the sheet material, and the sheet material under test may be moved linearly or within an X-Y coordinate system relative to the transducer assemblies.

Other aspects, definitions and features of the invention will become clear as the description to be considered in conjunction with the drawing continues.

BEST MODE FOR CARRYING OUT THE INVENTION

Figure 1:
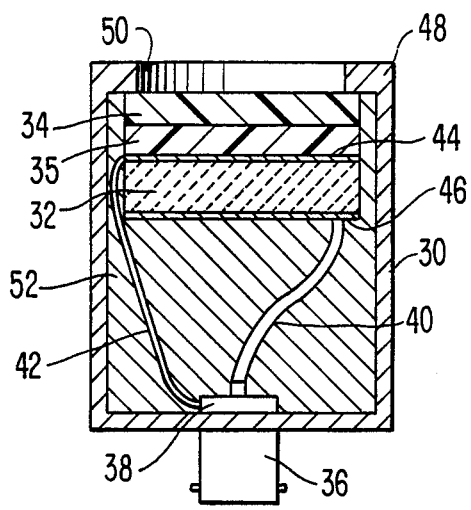
FIG. 1 is a schematic presentation, in elevation, of an ultrasonic transducer assembly.

FIG. 1 is a detailed illustration of the transducer or transducer assembly for use in a test procedure as discussed in connection with the system discussion to follow below. The transducer includes a housing 30 for supporting a piezoelectric layer 32, two impedance matching layers 34 and 35, and a connector 36 for electrical connection to external equipment, such as signal generator 14 (see FIG. 2A). A terminal 38 is supported by the connector, as illustrated, and a pair of conductors 40, 42 electrically connect the piezoelectric layer to the terminal at locations provided by metallic films 44, 46. The metallic films are applied as a coating to opposite sides of the piezoelectric layer.

The layers of impedance matching materials are bonded to each other and one face of the piezoelectric layer. The side of the piezoelectric layer to which the impedance matching layers are bonded becomes the radiating/receiving face of the transducer. The impedance matching layers provide a high efficiency transfer of ultrasonic energy between the piezoelectric layer and air.

The construction of the housing is such to provide an open interior. The transducer including a piezoelectric layer, impedance matching layers and terminals is mounted within the housing. A wall 48 defined by an inward extending lip provides a shoulder for support of the layers, and the opening 50 within the lip defines the source of the ultrasonic energy coupled by the impedance matching layers to air. The terminal 38 and connector 36 are supported on the end wall of the housing. The piezoelectric layer and impedance matching layers may be secured within the interior of the housing, adjacent the opening 50, by a potting material 52, or secured in some other conventional manner.

The piezoelectric layer 32 of the transducer is made from a piezoelectric ceramic, such as lead zirconate titanate or the like, having an acoustic impedance of about $3 \times 10^7$ Pascal-seconds-meter (PaS/M). The piezoelectric material having a slab-like form may be a commercially available material, such as the material designated either PZT-4 or PZT-5. One supplier of the material is Nittany Piezo Kinetics. Other piezoelectric materials with similar acoustic impedances may be used as well.

The acoustic impedance of a single one quarter wavelength thickness of impedance matching material may be calculated, as follows:

$$Z_L = \sqrt{Z_P Z_A}$$

where
$Z_L$ is the impedance of the matching layer,
$Z_P$ is the impedance of the piezoelectric layer, and
$Z_A$ is the impedance of ambient air.

Under circumstances that the impedance of the piezoelectric layer is about $3 \times 10^7$ PaS/M, the impedance of the matching layer may be determined utilizing the value of impedance for air of $4 \times 10^2$ PaS/M. Thus, the impedance of the matching layer is determined to be about $1.1 \times 10^5$ PaS/M. Materials having this value of acoustic impedance, or a value close to the calculated value, are not commonly available.

According to the invention, the matching impedance may be developed by multiple matching layers of materials that are commonly available. Under circumstances of a two layer system, for example, the first matching layer 35, the layer adjacent to the piezoelectric layer 32, is used to simulate an intermediate impedance which, then, can be matched to that of air by the second matching layer 34. In a specific embodiment of the invention the first matching layer is formed from a material with an acoustic impedance of approximately $3.1 \times 10^6$ PaS/M. The first matching layer may be made from a one quarter wavelength acrylic sheet (PLEXIGLAS) or an equivalent material with a similar acoustic impedance, also of approximately $3.1 \times 10^6$ PaS/M. When a first matching layer of a one quarter wavelength acrylic sheet (PLEXIGLAS) is bonded to a piezoelectric material, it simulates an acoustic impedance of $3.2 \times 10^5$ PaS/M. A second one quarter wavelength layer with an approximate impedance of $1.1 \times 10^4$ PaS/M may then be used to match the impedance of the first matching layer to that of air.

The numbers used in the calculation according to equation (1) are nominal values, and it has been found that the materials of the matching layers may be replaced with equivalent materials having comparable characteristics. Thus, the one quarter wavelength acrylic sheet (PLEXIGLAS) may be replaced by a layer of an equivalent material, such as an acrylic resin (LUCITE), polystyrene or nylon.

The acoustic impedance of commonly available homogeneous solids and liquids are 50 to 100 times larger than the desired acoustic impedance for the second matching layer, as calculated above. On the other hand, the acoustic impedance of gases are typically many orders of magnitude smaller than the desired value of acoustic impedance. Thus, according to the invention, the material for the second matching layer must be inhomogeneous in the sense that the material must contain significant portions of gas and have the characteristics with regards to absorption and scattering loss, as well as the construction of walls of the gas cells and dimension of the gas cells. Thus, to reduce absorption and scattering loss in the second matching layer, the gas cells must be both closed and uniformly distributed. In addition, the walls of the gas cells should be made from materials with low ultrasound absorption characteristics. Further, the dimension of the cells must be much smaller than the wavelength of the ultrasound. According to the invention, it has been found that polystyrene foam, of the type commonly available as a domestic thermal insulation, meets the requirement of cell size, as well as cell construction and distribution, and may be clearly distinguished from foams of other materials, such as silicone, rubber, and open cell foams, each of which exhibit a high ultrasonic attenuation resulting in an overall loss of efficiency of the transducer assembly. This overall loss of efficiency is because the foam layer of these last-mentioned materials has an absorption characteristic greater than that of polystyrene. Further, the foam layer has a surface roughness proportional to its cell size. If the cell size is comparable to the wavelength of ultrasonic energy in air, the ultrasonic energy transmitted and received at different areas along the surface will have significantly different phases resulting in severe loss of transducer efficiency. On the other hand, if the cell size is considerably smaller than the wavelength of ultrasonic energy in air, such as that of polystyrene foam the ultrasonic energy transmitted and received at different areas along the surface of the second matching layer will have substantially the same phase.

Polystyrene foams of different density are commercially available. A polystyrene foam with a density of about 30.88 grams/cm$^3$ will have an acoustic impedance of approximately $3.3 \times 10^4$ PaS/M which is comparable to the desired value of $1.1 \times 10^4$ PaS/M. According to the invention a high-efficiency, air-coupled transducer can be assembled from a piezoelectric layer 32, a layer of acrylic sheet (PLEXIGLAS) 35 of some wavelength and an impedance matching layer 34 of one quarter wavelength polystyrene foam.

As previously discussed, regarding the substitution of material for the one quarter wavelength acrylic sheet (PLEXIGLAS) layer, the polystyrene foam may be replaced by foams having similar characteristics although of different density.

In operation, the transducer assembly vibrates at the resonant frequency of the composite including the first matching layer 35, and the piezoelectric layer 32. The second matching layer 34 is a one quarter wavelength layer at this frequency of resonance. At high frequency, the operating frequency of the transducer assembly may be substantially altered by replacing the first matching layer with a matching layer of different thickness. At lower frequencies, however, the piezoelectric layer 32 has substantial mass so that the resonant frequency is not significantly altered by a change in the thickness of the first matching layer. However, a change in the thickness of the second matching layer from that of one quarter wavelength will result in significant loss of efficiency.

The physical dimensions of piezoelectric layer 32 may be chosen so that one of its radial modes of vibration overlaps the thickness resonance of the composite including the first matching layer 35 and the piezoelectric layer. This will result in significantly larger amplitude of vibration which may be coupled to air by the second matching layer 34. The net result is that a considerably higher power can be coupled to air, and ultrasound energy of very low intensity is capable of being detected from air with good signal to noise ratio.

Transducer assemblies, with matching layers operating in the thickness mode have a narrow bandwidth. A wider bandwidth transducer assembly may be formed by a choice of a radial-mode of vibration that is close to but does not overlap the thickness resonance of the composite including the first matching layer 35 and the piezoelectric layer.

A table of specifications is set out below:

| Piezoelectric layer | | Plexiglass | Foam | Frequency |
| --- | --- | --- | --- | --- |
| Thickness | Diameter | Thickness | Thickness | (in KHz) |
| 0.125 | 1.5 | 0.06 | 0.022 | 420 |
| 0.5 | 1.5 | 0.12 | 0.115 | 95 |
| 0.5 | 0.75 | 0.25 | 0.115 | 85 |
| 0.125 | 0.75 | 0.12 | 0.115 | 95 |

The thickness and diameter of the piezoelectric layer, and the thickness of both the acrylic sheet (PLEXIGLAS) and foam layers is in inches. As to mode, the mode of the first two lines of data is a thickness mode, the mode of the third line of data is a mixed mode, and the mode of the fourth line of data is a radial mode.

Figure 5:
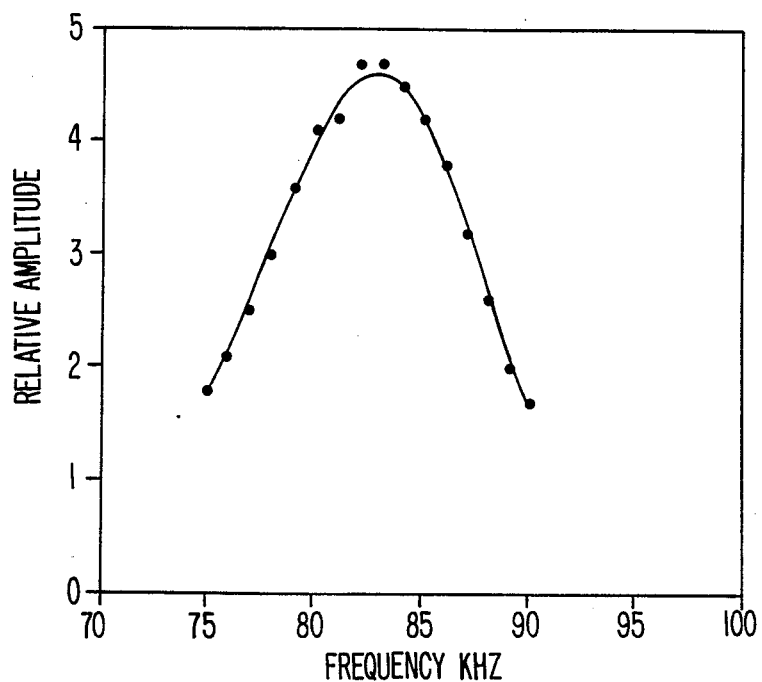
FIGS. 5 and 6 each illustrate a graph which plots the output from a transducer at various frequencies of operation.
Figure 6:
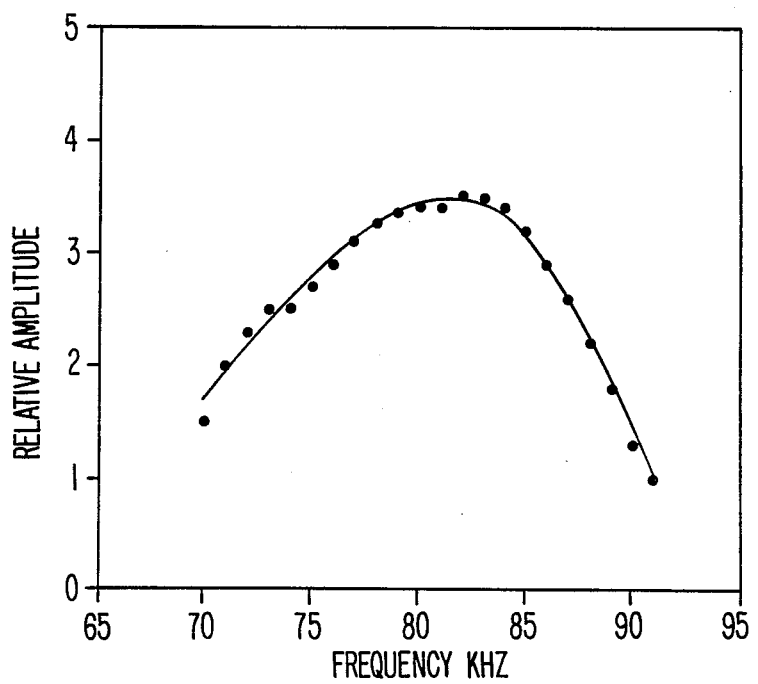

FIGS. 5 and 6 illustrate a plot of frequency response characteristics for two embodiments of transducer assembly. In FIG. 5, the plot of frequency (KHz) to relative amplitude is derived from a transducer assembly including a piezoelectric layer 32 having a thickness of 0.5 inch and a diameter of 0.75 inch, a first matching layer 35 of plexiglass having a thickness of 0.12 inch and a second matching layer 34 of polystyrene foam having a thickness of 0115 inch. According to FIG. 6, the relative amplitude of the plot is reduced at the peak frequency (compare FIGS. 5 and 6) by using a first matching layer of an acrylic sheet (PLEXIGLAS) having a thickness approximately twice the thickness of the plexiglass used in the operation plotted in FIG. 5.

The invention may be used in connection with testing procedures for the determination of the strength of a homogeneous material, such as a sheet or web of paper (hereafter "sheet"). A system and apparatus for the generation and detection of ultrasound in the sheet, and its inspection, may be seen in FIG. 2A. By use of the system and apparatus to be described, through use of an air-coupled transducer assembly configuration to measure the velocity of ultrasound in a sheet (the sheets 10a, 10b to be discussed) attains the end of better yield and quality of product through improved process control.

A sheet 10a is illustrated in position for test. Testing may be carried out on individual sheets, but preferably the sheet will be in the form of a continuous web, such as the web illustrated in FIG. 2B moved by structure (not shown in FIG. 2A) along a conveyor path through a testing location. Each increment of the length of the sheet may be subject to test at the testing location as the sheet is moved in one coordinate direction. Movement of the sheet is illustrated by the arrow 12.

Inspection of the sheet at the testing station may be incorporated in an on-line measurement method during the papermaking process and may be carried out by an electrical system including a signal generator 14, a transducer 16 including a layer of piezoelectric material for transforming electrical energy to ultrasonic energy, and a coupling medium 18 for efficient coupling of ultrasound into air. The transducer including the piezoelectric layer and coupling medium including two matching layers may be referred to as a "transducer assembly."

The signal generator functions to produce an electric signal in the form of an oscillatory burst of energy over a relatively short time duration at the resonant frequency of the transducer assembly. A signal generator, such as a Velonex Model 570, with a Model 350-12 Plug-in, may be used. An inspection operation may be carried out using an oscillatory burst of energy at a frequency of 85 KHz, over a 60 sec duration which causes the transducer assembly 16, specifically the piezoelectric layer to vibrate. The resulting ultrasonic wavefront is coupled through air to the sheet and causes the sheet to vibrate.

The ultrasound propagates in a direction which essentially is normal to the surface of the coupling medium 18 thereby to strike sheet 10a at some angle of incidence. The preferred magnitude of the angle of incidence is dependent upon several factors including the thickness of the material, in this instance the sheet under inspection, the frequency of operation of the signal generator and the desired wave mode generated in the plane of the sheet.

Several ultrasonic wave modes are generated in the plane of the sheet. One wave mode, the S0 wave mode, is the longitudinal plate wave mode. Since the S0 wave mode has the highest velocity in a Kraft paper at about 90 KHz it can be discriminated as the first wave mode to arrive at a detector site defined by a second transducer assembly. The ultrasonic vibrations in the form of a tone burst propagate in the sheet as leaky Lamb waves radiating ultrasonic energy to the surrounding air. The second transducer assembly for detection of ultrasound radiating from the sheet in the form of a propagating tone burst comprises a separate, distinct assembly situated to receive the ultrasonic energy from the sheet.

The time from initiation of the ultrasonic burst to receipt of a signal from the material under test signal can be accounted for, as follows: (1) time for the ultrasound to travel from transducer assembly 16 to the sheet 10a, (2) time for the ultrasound to travel from the point of entry to the sheet to the point of emergence from the sheet, and (3) time for the radiated ultrasound to travel from the sheet to the second transducer assembly illustrated in FIG. 2A by the numeral 20. Thus, a measurement of time between transmission and reception of the ultrasound, minus transport time through air gaps is the propagation time of the ultrasound in the sheet. By accurately measuring the distance between the points of entry and emergence, the velocity of the ultrasound may then be determined by dividing distance by propagation time. Paper strength may be calculated from the velocity data.

Figure 2A:
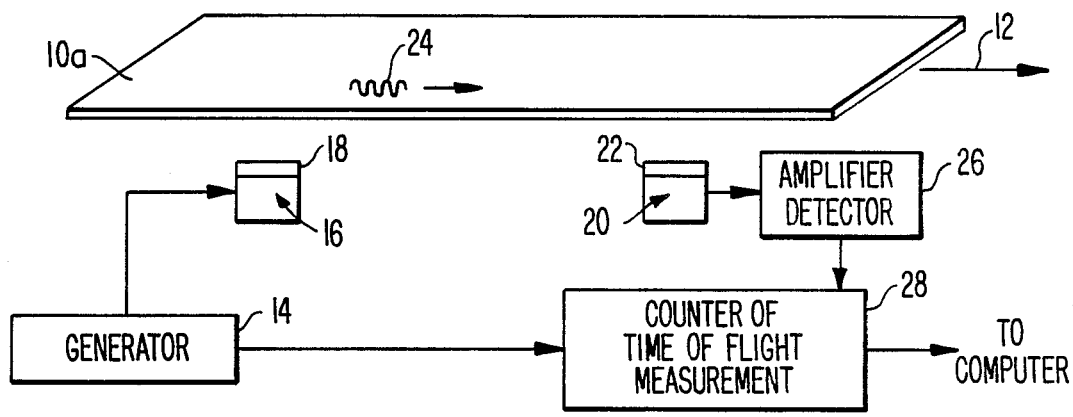
FIG. 2A is a perspective, schematic presentation of a non-contact system incorporating the ultrasonic transducer of FIG. 1 for measuring velocity of ultrasound in paper.
Figure 3:
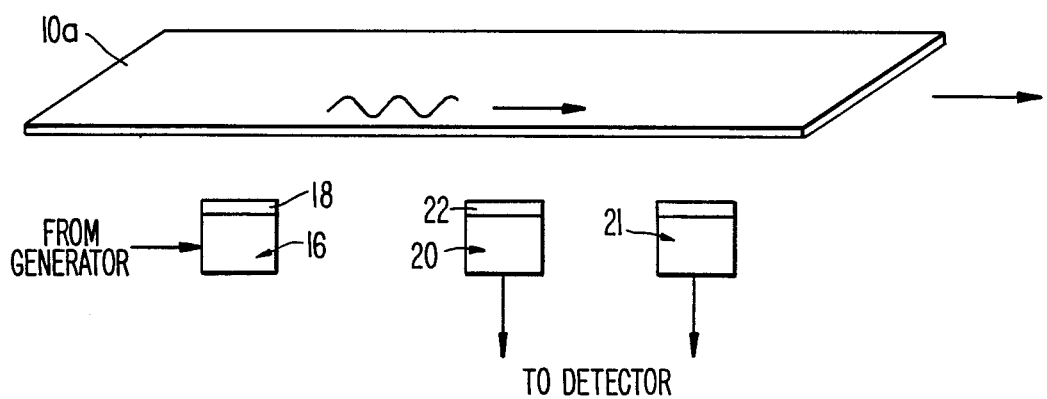
FIG. 3 is a perspective, schematic presentation of a non-contact system incorporating a transmitter transducer and two receiver transducers for measuring velocity of ultrasound in paper.

Perhaps a better measurement of the velocity of the ultrasonic vibrations may be obtained through implementation of a system illustrated in FIG. 3. The particular system generally includes the structure of FIG. 2A, and includes a second receiver transducer assembly 21. The operation carried out in FIG. 3 is one of measuring a difference in time ($t_2 - t_1$) recorded by the transducer assemblies 21 and 20, respectively. This measurement is more accurate than the difference in time ($t_1 - t_0$) measured from the time of the oscillatory burst of energy, at $t_0$, from generator 14 to the time, $t_1$, recorded by transducer assembly 20. The improvement follows from the fact that the system operation of FIG. 3 does not require the subtraction of time for the oscillatory burst to travel across the air gaps which is affected by temperature and humidity at the air gaps.

The second transducer assembly 20, FIG. 3, and the third transducer assembly 21, like first transducer assembly 16, is located in a position that the ultrasonic energy propagated from the sheet is directed substantially normal to its receiving surface. More particularly, the second transducer assembly includes a transducer 20 including a layer of piezoelectric material to transform the airborne ultrasound into electrical energy for detection and a coupling medium 22 for efficient coupling of the ultrasound between the ultrasonic transducer and air. The third transducer assembly is similarly formed. A longitudinal ultrasonic plate wave 24 is illustrated in FIG. 3 as having been generated in the sheet 10a. As indicated, the velocity of the ultrasound in the sheet is to be detected and, as has been discussed, the strength of the sheet is related to the velocity of the longitudinal ultrasonic plate wave mode which shall propagate in the plane of the sheet. These modes are dispersive and only the velocity of the longitudinal plate wave mode at frequencies around 90 KHz, a relatively low frequency, is related to strength. The distance, between the first and second transducer assemblies, FIG. 2A, and the second and third transducer assemblies, FIG. 3, is selected so that the longitudinal plate wave mode can be easily discriminated by provision of a good signal-to-noise ratio.

The ultrasonic energy emitted from sheet 10a is transformed to an electrical signal to be detected by a detector 26. The ultrasonic energy coupled between the transducer assemblies will be attenuated by losses at the air-object boundaries. However, the efficiency of the overall system of operation is improved, possibly several hundred times over conventional transducer assemblies thereby to permit sensitive inspection of objects even though these losses may be considerable. An amplifier which may be a part of the detector is provided to amplify the electrical signal. The system also includes a counter 28 for time of flight measurement.

According to the FIG. 2A illustration, generator 14 is electrically connected to the first transducer assembly 16 and counter 28, the latter of which is electrically connected to the second transducer assembly 20, through detector 26. The counter, in turn, is connected to a computer (not shown). A similar electrical connection will be provided for the FIG. 3 system.

While the transducer assemblies are illustrated on the same side of sheet 10a and below the sheet, for example, the transducer assemblies, equally as well, may be located above the sheet or on opposite sides of the sheet. In any arrangement, the transducer assemblies are non-contact assemblies spaced about 1 inch or more from the surface of the sheet to provide an airborne ultrasonic measurement.

A source of inefficiency in non-contact, air-borne ultrasonic inspection is the insertion loss due to the difference in acoustic impedance between the material under test and air. In practice, only a small fraction of the ultrasonic wavefront enters and propagates in the material under test, the sheet 10a for example, with the remainder of the wavefront being reflected from the surface of the sheet. To increase efficiency in operation of the apparatus, the effective impedance mismatch between the sheet and air should be reduced. The impedance mismatch may be reduced in a manner as described below regarding the apparatus of FIG. 2B.

Figure 2B:
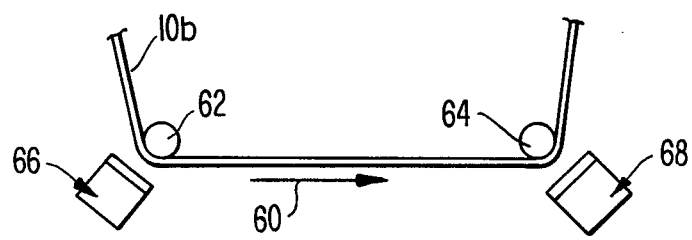
FIG. 2B is a schematic presentation, like FIG. 2A, wherein ultrasonic signals are generated and detected at curved portions of the paper being tested.

Reference now may be made to FIG. 2B which illustrates a technique of generating and detecting ultrasonic signals at locations of a sheet 10b moving in the direction of directional arrow 60. The sheet 10b may be an endless web entrained about rolls 62, 64 during a part of the conveyer path. A first transducer assembly 66 is located in proximity to roll 62, particularly at a location at which sheet 10b makes a curved pass, and a second transducer assembly 68 is located in proximity to roll 64, particularly at a location at which sheet 10b makes another curved pass. The transducer assemblies 66, 68 may be likened to the transducer assemblies 16, 20 and are connected in an electrical system including a signal generator, detector and counter, such as illustrated in FIG. 2A. The particular arrangement of the transducer assemblies in FIG. 2B serves to reduce the mismatch in effective impedance between the sheet and air to provide a system operation having an efficiency which is significantly improved from that of FIG. 2A. Similarly, a three transducer system, as illustrated in FIG. 3, may be reconfigured by positioning transducers over curved passes of a web. By locating transducer assemblies in the machine direction, and additional transducer assemblies in a cross-machine direction (not shown, but as should be understood) it will be possible to determine strength of the sheet in both directions, and determine squareness in the strength of paper as well. An array of transducers positioned across the web can be used to determine uniformity of strength in the cross-machine direction.

Figure 4A:
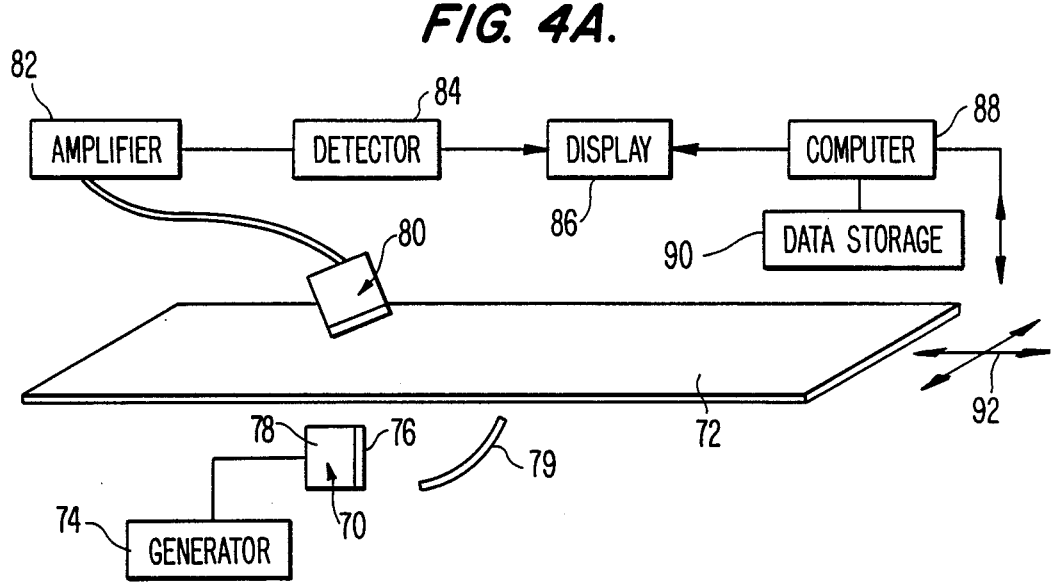
FIG. 4A is a perspective, schematic presentation of a non-contact system, similar to that of FIG. 2, for inspection of a sheet product.

Turning now to FIG. 4A, there is a schematic showing of apparatus for inspecting composite materials using non-contact, air-coupled ultrasonic attenuation measurement techniques. Defects in the composite may be detected and located by comparing measured attenuation to a reference level. In operation, an air-coupled transducer assembly generates ultrasonic vibrations in the composite under test by transmitting ultrasound through air into the test piece. Ultrasound emitted from the composite is received by a second air-coupled transducer assembly and processed to evaluate the quality of the product under inspection. The second transducer assembly may be a separate, distinct assembly situated to receive the ultrasonic energy from the product or, in principle, it may be the receive capability of the first transducer assembly. To this end, if the first transducer assembly is to function as both a transmitter and receiver the transmission of ultrasonic energy must be discontinuous to also permit reception. A variation in the level of the detected signal is an indication of the presence of a defect in the product under test.

According to FIG. 4A, a first transducer assembly 70 is located relative to one side of a composite 72 in the form of a sheet product. The transducer assembly, like the transducer assembly 16, is excited by a tone burst from signal generator 74. The signal generator may be of the type heretofore described. The system of FIG. 4A differs from the system of FIG. 2A in that the ultrasonic wavefront to be conducted by air to the composite to generate ultrasonic vibrations in the composite may be concentrated by a deflector 79. As previously discussed the coupling medium for coupling the ultrasonic energy into air comprises matching layers 76 for matching the impedance of piezoelectric layer 78 and air. This structure and the electrical connection of the transducer assembly and signal generator has been discussed in the discussion directed to FIG. 2A. The ultrasonic wavefront propagating in the composite radiates ultrasonic signals to the surrounding air. A second transducer assembly 80 is located on the opposite side of the composite. The second transducer assembly receives signals which are processed to assess product quality. The processing apparatus includes an amplifier 82, if needed to amplify the signal, detector 84, display 86, computer 88 and data storage device 90. Any defect including holes, pipes, delaminations and inhomogeneities serve to modify the ultrasonic vibration of the material, and, thus, the emitted signals from the composite. Changes in attenuation of the ultrasonic signal indicate the presence of defects in the composite.

During a typical inspection, the composite under test is positioned between the first and second transducer assemblies 70, 80, each located within several inches of the surface of the composite. The composite may be moved by a scanner (not shown) in the X-Y coordinate directions as indicated by arrows 92. The detector circuitry records the level of ultrasound corresponding to the portion of composite currently in the sound path. If the composite contains a defect, a change in the level of ultrasound is detected. The location, size and severity of each defect can be indicated.

Figure 4B:
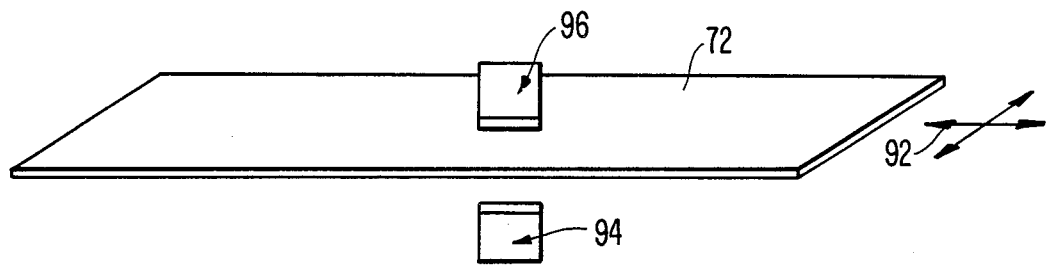
FIG. 4B is a schematic presentation, like FIG. 4A, without incorporation of a focusing arrangement.

In the FIG. 4A system illustration, deflector 79 serves to improve the signal to noise ratio and resolution of all detectable defects by concentrating the ultrasound. This result may also be obtained by using transducer assemblies of small cross section. The incident ultrasound may also be oriented at an angle to generate resonant Lamb waves in the composite under test. The test setup envisions that the second transducer assembly 80, located on the opposite side of the composite, is positioned at an angle identical to the incident angles. Turning to FIG. 4B, there is illustrated a pair of assemblies 94, 96 operating at about 400 KHz. The system of FIG. 4A can detect delaminations and a lateral void as small as 0.08" diameter in composite materials. It has also been demonstrated that more efficient transducer assemblies of smaller cross section can detect composite defects without any focusing arrangement.

I claim:

1. A transducer assembly for use in a non-contact system for measurement of properties and detection of imperfections of the internal portion of materials including:

(a) a layer of piezoelectric material having the capability of transforming electrical energy into ultrasonic energy at a resonant frequency of the transducer assembly;

(b) a first matching layer of one quarter wavelength bonded to said piezoelectric layer; said first matching layer simulating an intermediate impedance;

(c) a second matching layer composed of a closed gas cell foamed material, said second matching layer sized at one quarter wavelength layer and bonded to the side of said first matching layer further from said piezoelectric layer, the gas cells of said foam being uniformly distributed throughout said second matching layer and very much smaller than the wavelength of the ultrasound energy, said second matching layer matching the simulated impedance of said first matching layer to the impedance of air for optimizing the coupling efficiency of said ultrasound energy into ambient air and airborne ultrasound adapted to be emitted from said materials from ambient air; and (d) said layer of piezoelectric material sized dimensionally in relation to said first and second impedance matching layers so that one of the radial modes of vibration of said layer of piezoelectric material overlaps the thickness resonance of the composite of said first and second impedance matching layers.

2. The transducer assembly of claim 1 wherein said first matching layer is a layer of material selected from the group consisting of an acrylic sheet, an acrylic resin, nylon and polystyrene, and said second matching layer is selected from the group consisting of polystyrene, polyurethane and a thermostatting resin that may be foamed, such as an acrylic resin and nylon.

3. The transducer assembly of claim 2 wherein said second matching layer is polystyrene.

4. The transducer assembly of claim 2 wherein said first matching layer is acrylic sheet.

5. The transducer assembly of claim 1 including a metallic film layer coating opposite sides of said piezoelectric material, and a conductor connecting each film layer to a terminal adapted to be connected to a source of electrical energy.

6. The transducer assembly of claim 5 including a housing with an open interior and a transmitting/receiving face at one end, said second matching layer disposed across said face, and means for substantially encasing said piezoelectric material and matching layers in said housing.

7. The transducer assembly of claim 1 wherein said piezoelectric material has an impedance of about $3 \times 10^7$ PaS/M, said first matching layer has an impedance of about $3.1 \times 10^6$ PaS/M, and said second matching layer has an impedance of about $1.1 \times 10^4$ PaS/M.

8. A transducer assembly for use in a non-contact system for measurement of properties and detection of imperfections of the internal portion of materials including:

(a) a layer of piezoelectric material for transforming electrical energy into ultrasonic energy at a resonant frequency of the transducer assembly;

(b) a first matching layer of a single piece of impedance matching material, said first layer sized at one quarter wavelength of said resonant frequency and bonded to said layer of piezoelectric material, said impedance matching material of said first layer being adapted of simulation an intermediate impedance;

(c) a second layer of a second different impedance matching material, said second layer also sized at one quarter wavelength of said resonant frequency, said second layer disposed on and bonded to the side of said first layer further from said piezoelectric layer, said second different impedance matching material of said second layer being composed of a single material which is adapted to match the simulated impedance of said first layer to the impedance of air for optimizing the coupling efficiency of (i) said ultrasonic energy into ambient air or (ii) airborne ultrasonic energy emitted from the materials under measurement from ambient air, said material of said second layer being a closed cell foam with very small uniformly distributed gas cells so that the absorption and scattering loss characteristics of said second impedance matching layer are reduced; and (d) said layer of piezoelectric material sized dimensionally in relation to said first and second impedance matching layers so that one of the radial modes of vibration of said layer of piezoelectric material overlaps the thickness resonance of the composite of said first and second impedance matching layers.

9. A transducer assembly for use in a non-contact system for measurement of properties of and detection of imperfections in the internal portion of materials including:

(a) a layer of piezoelectric material for transforming electrical energy into ultrasonic energy at a resonant frequency of the transducer assembly;

(b) a first matching layer of a single piece of impedance matching material, said first layer sized at one quarter wavelength of said resonant frequency and bonded to said layer of piezoelectric material, said impedance matching material of said first layer being adapted to simulate an intermediate impedance;

(c) a second layer of a second different impedance matching material said second layer also sized at one quarter wavelength of said resonant frequency, said second layer disposed on and bonded to the side of said first layer further from said piezoelectric layer, said second different impedance matching material of said second layer being composed of a single material which is adapted to match the simulated impedance of said first layer to the impedance of air for optimizing the coupling efficiency of (i) said ultrasonic energy into ambient air or (ii) airborne ultrasonic energy emitted from the materials under measurement from ambient air and vibrate in both the thickness and mixed mode; and (d) said layer of piezoelectric material sized dimensionally in relation to said first and second impedance matching layers so that one of the radial modes of vibration of said layer of piezoelectric material overlaps the thickness resonance of the composite of said first and second impedance matching layers.

* * * * *